United States Patent [19]
Staples et al.

[11] Patent Number: 5,289,715
[45] Date of Patent: Mar. 1, 1994

[54] VAPOR DETECTION APPARATUS AND METHOD USING AN ACOUSTIC INTERFEROMETER

[75] Inventors: Edward J. Staples, Thousand Oaks; Gary W. Watson, Newbury Park, both of Calif.

[73] Assignee: Amerasia Technology Inc., Westlake Village, Calif.

[21] Appl. No.: 791,786

[22] Filed: Nov. 12, 1991

[51] Int. Cl.$^5$ ............................................. G01N 29/02
[52] U.S. Cl. ................................. 73/24.01; 73/31.06
[58] Field of Search ................ 72/24.01, 24.06, 31.06, 72/23.40, 23.41, 23.42; 422/89

[56] References Cited

U.S. PATENT DOCUMENTS

| | | | |
|---|---|---|---|
| 3,677,066 | 7/1972 | King | 73/31.05 |
| 4,055,072 | 10/1977 | Fletcher et al. | 73/24.01 |
| 4,312,228 | 1/1982 | Wohltjen | 73/23.31 X |
| 4,361,026 | 11/1982 | Muller et al. | 73/24.01 |
| 4,711,765 | 12/1987 | Cates | 422/70 |
| 4,759,210 | 7/1988 | Wohltjen | 73/31.07 |
| 4,895,017 | 1/1989 | Pyke | 73/24.06 |
| 5,012,668 | 5/1991 | Haworth | 73/24.06 |
| 5,076,094 | 12/1991 | Frye et al. | 73/24.01 X |
| 5,130,257 | 7/1992 | Baer et al. | 73/DIG. 4 |

FOREIGN PATENT DOCUMENTS 282115 8/1990 Fed. Rep. of Germany ..... 73/24.06

OTHER PUBLICATIONS

D'Amico, A. et al. *Palladium-Surface Acoustic Wave Interaction for $H_2$ Detection.* in Appl. Phys. Lett. vol. 42, No.3, pp. 300-301, Aug. 1, 1982.

Primary Examiner—Hezron E. Williams
Assistant Examiner—Joseph W. Roskos

[57] ABSTRACT

A detector and method for identifying a chemical vapor and determining its concentration in the ambient atmosphere. The chemical detector apparatus preferably includes a means of collecting vapors in one atmosphere and transferring the vapors by injection into a chromatographic separation column. The exit of the separation column is confined by a nozzle which causes the vapors to be focused into a specific area of an acoustic wave interferometer wherein standing waves are created by constructive interference of waves reflected from a plurality of reflecting elements. Identification of vapor species is by a combination of timed adsorption rate peaks and temperature programmed desorption rates of the individual vapor species.

8 Claims, 6 Drawing Sheets

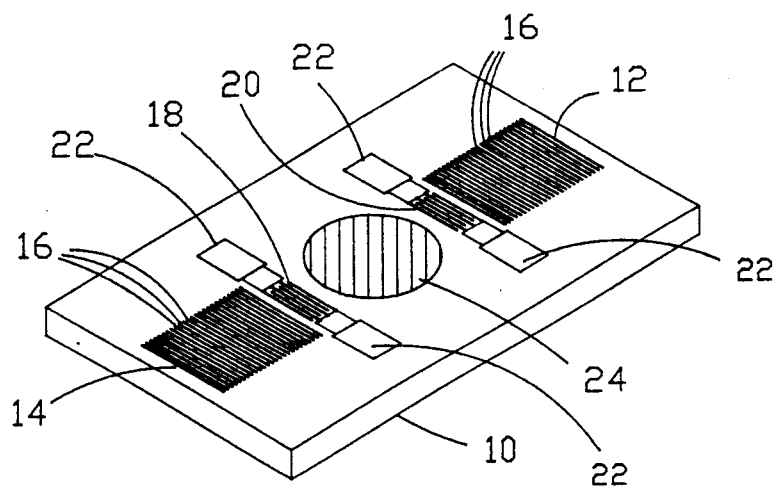
Fig. 1
Fig. 2
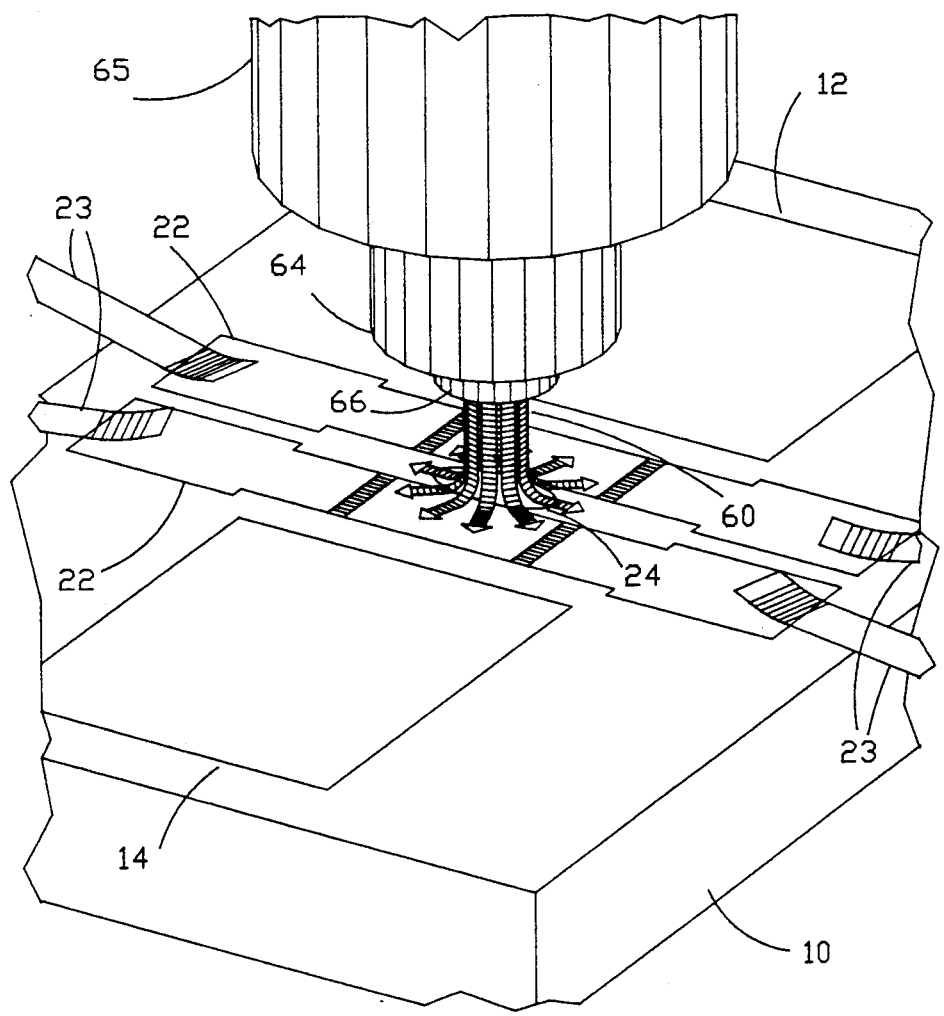

VAPOR DETECTION APPARATUS AND METHOD USING AN ACOUSTIC INTERFEROMETER

FIELD OF THE INVENTION

The invention is in the analysis and detection of identifiable vapor elements, and more particularly, to a sensor and method in which a physical parameter associated with the sensor changes in a defined manner upon exposure to an unknown vapor, permitting identification of the individual vapor elements.

BACKGROUND DESCRIPTION OF PRIOR ART

In the analysis of chemical vapors there is frequently a need to detect extremely small trace amounts of a specific vapor amongst a background of different chemical species. Examples are the detection of contraband aboard the cargo of vessels being inspected by the United States Coast Guard and the detection of leaking explosive or dangerous chemicals at depositories thereof. Automated or portable testing apparatus for this purpose has generally not been available. Further, existing detectors are only able to detect chemical species at concentrations well above their ambient vapor concentrations and thus lack sufficient sensitivity.

Chemical sensors have been developed that physically change upon exposure and contain absorbing polymers selected for their affinity to absorb a group of related chemical species. One type, surface acoustic wave delay line sensors, are the most developed and readily available, for example, one commercial supplier is Microsensor Systems, Inc., Fairfax, Va.

A method and apparatus for using A SAW device to detect a vapor is disclosed by H. Wohltjen in U.S. Pat. No. 4,312,228, issued Jan. 26, 1982. As described therein, the SAW device comprises a piezoelectric element having a surface coated with a polymer material selected to absorb and react with the chemical to be detected. Interaction of the chemical with the material coating of the sensing element alters one or more properties of a surface acoustic wave, and the electrodes on the piezoelectric element detect the altered wave, producing an electrical signal.

Another apparatus and method for detection and identification of chemical vapors is disclosed in U.S. Pat. No. 4,895,017. As described therein a plurality of surface acoustic wave (SAW) devices, each coated with a selected polymer material are exposed to the vapor to be analyzed. In this invention a predicted time constant (or rate) of diffusion into the polymer coating is used to identify the different chemical species. To quantitatively identify specific chemical species present in vapors an array of SAW sensors with different polymer coatings may be exposed and a pattern recognition technique utilized to identify specific species. This is described in a paper entitled "Correlation of Surface Acoustic Wave Device Coating Responses With Solubility Properties and Chemical Structure" by D. S. Ballentine, Jr., S. L. rose, J. W. Grate, and H. Wohltjen, published in Analytical Chemistry, Vol. 58, P. 3058, December 1986.

A further patent using multiple polymer coated dispersive delay lines is disclosed by J. Haworth in U.S. Pat. No. 5,012,668, issued May 7, 1991. The use of specific absorbant polymers to sensitize the surface of a piezoelectric crystal and induce a phase or amplitude variation in a traveling acoustic wave is common to all of the prior art and this approach severely limits the performance of these vapor detectors. Multiple polymer films dilute the vapor samples and thereby limit the amount of vapor that can be detected by each film. Also, practically any type of film applied to the surface of a piezoelectric crystal introduces noise which reduces sensitivity further. None of the prior art provides an efficient method of transporting the vapors being analyzed to the surface of the sensing crystal. Nor does any of the prior art utilize the desorption characteristics of vapor species to identify individual vapor species.

There are Four problems with the procedures used for identifying chemical substances in the above described tests. First, the prior methods rely upon determination of the rate of diffusion and or equilibrium concentration of a chemical vapor absorbed into a coating on the surface of a SAW device. The time to identify a chemical species by chemical absorption of that species into a polymer film is too long for applications such as high speed chromatography, which require identification to be in seconds or milliseconds.

Second, previous polymer coated sensors and sensor arrays require that they be coated uniformly to insure unbiased readings. This requires that input vapor elements be diluted and divided between the absorbing polymer coatings equally. In many cases only trace amounts of material are available and therefore cannot be equally exposed to the sensors without an undesirable reduction in the sensitivity of the vapor detection apparatus.

Third, previous sensors do not interact directly with a well defined gas jet stream and require a manifold or distribution system to pass vapors to be detected to the acoustic sensor containment vessel, typically a vented TO-8 style integrated circuit package. This allows vapor containing gas to contact a significant amount of equal temperature surface areas not associated with the detection process. These surfaces adsorb and trap condensible vapors and reduce the amount of vapor material which can reach and be absorbed by the sensor's polymer coating.

Fourth, previous sensors require polymer coatings selective to a given species. These coatings introduce dissipation, attenuation and loss into the propagation path of the surface wave device and this causes lower signal to noise in the measurement of the surface wave velocity, phase, or amplitude. The low specificity of the polymer coating and sample dilution together increased noise and decreased sensitivity can cause an unacceptable number of false alarms.

OBJECTS AND ADVANTAGES

It is the object of the present invention to rapidly detect a chemical substance present in relatively low trace concentrations within an ambient atmosphere and to determine its nominal concentration in said atmosphere. It is a further object to identify the chemical substance or a known group of substances.

Other objects and advantages of the present invention are as follows:

(a) to detect and measure the mass and rate of mass change due to adsorbed vapor species on the surface of an acoustic interferometer.

(b) to identify specific vapor species according to their adsorption characteristics within a thermal gradient produced between a relatively hot and focused vaporous gas jet stream flow from a nozzle and a temperature controlled acoustic interferometer.

(c) to identify specific vapor species according to their desorption characteristics produced by heating a piezoelectric acoustic interferometer containing adsorbed or absorbed vapor species.

(d) to detect and identify a chemical substance by adsorption of the condensible vapor mass within the effluent of a chromatographic separation column using an acoustic wave interferometer adsorption sensor. A further object is to detect and identify individual chemical vapors by a chromatographic separation measurement using the adsorption rate of each vapor species to determine the time for each species to pass through the chromatographic separation column.

(e) to collect vapor species from a test atmosphere and to cause said species to adsorb on the surface of the acoustic interferometer without diluting the samples. A further object is increase vapor detection sensitivity by focusing the adsorbed vapor species onto a small and localized area of the interferometer surface by means of an effluent gas jet nozzle.

An advantage of the present invention is that polymer coatings on the SAW sensor are not required. Further advantages are (1) the acoustic sensor interacts directly with the effluent gas flow stream of a chromatographic capillary column (2) Adsorption and desorption of effluent species is controlled by a programmed temperature control of the acoustic wave sensor which creates a temperature gradient between the capillary effluent gas flow and the surface of the acoustic wave device, and (3) a folded path acoustic interferometer maximizes the sensitivity to adsorbed vapors from a focused gas stream by repeatedly reflecting acoustic waves to form localized acoustic standing waves within the adsorbed vapor species.

SUMMARY OF THE INVENTION

The invention relates to a method and apparatus for detecting, identifying and quantifying the constituent chemical elements within a vapor. In accordance with the present invention, apparatus is provided for performing high speed detection and identification of vapor species based upon the differing vapor pressure of each vapor species within a confined and focused high temperature gas stream. The apparatus includes a temperature programmed vapor preconcentrator for trapping condensable vapor species, a multi-port valve, a temperature programmed focusing trap injector, a temperature programmed chromatographic capillary column, an acoustic wave interferometer for detecting adsorption and desorption of vapor species, a thermoelectric heating and cooling element for controlling the temperature of the acoustic interferometer sensor, and an electronic system controller.

It is an object of this invention to provide a means of sampling an ambient environment and determining its constituent parts. Further it is an objective of this invention to provide an apparatus capable of detecting trace elements with high specificity and sensitivity.

It is another objective of this invention to provide a highly sensitive and near real time chromatographic sensor for monitoring the condensible vapors within the effluent vapor of a chromatographic separation column by creating a temperature gradient between an effluent gas stream nozzle and the acoustic wave sensor.

It is another objective of this invention to provide a quantitative and specific desorption measurement sensor for characterizing vapor species according to their rate of desorption from a temperature programmed surface of a SAW device.

It is another objective of this invention to provide an apparatus and method for sampling condensible vapor species in a test atmosphere and transferring said condensed vapor species to a chromatographic separation column and vapor detector which use with a specific carrier gas different from the sampled test environment.

It is another objective of this invention to provide a method of quantifying the total amount of specific condensible vapor species within a test atmosphere, the condensation or adsorption rate of each species, and desorption rate of each species.

The invention has the advantages of a folded path acoustic wave interferometer vapor sensor, which concentrates the acoustic wave energy into standing waves within a localized area, and an efficient vapor collecting apparatus for efficiently extracting condensible vapors from ambient environments. Surface wave velocity changes are proportional to the mass and thickness of adsorbed and condensed vapor species. For a given vapor species sensitivity and detectability are enhanced by focusing condensable material from a nozzle onto the localized standing waves of an acoustic interferometer. The invention of a focused acoustic wave interferometer vapor sensor allows vapor detection of condensible vapors as small as $1 \times 10^{-14}$ gram which is an improvement in the sensitivity of Prior Art sensors by more than 1000.

Further advantages are increased reliability, reduced maintenance, and lower manufacturing cost because the sensor does not require absorbant polymer coatings which can fail by becoming contaminated or overloaded with absorbed vapors.

Still further advantages of the invention over Prior Art are obtained by controlling the surface temperature of the acoustic interferometer relative an ambient atmosphere. Reversing the thermal gradient between the surrounding atmosphere and the surface of the acoustic interferometer allows insitu cleaning of adsorbed vapors. Furthermore, by measuring the desorption rate of adsorbed vapors in response to a linear rise in the acoustic interferometer sensor, specific vapors can be identified by their individual desorption temperature and desorption rate.

BRIEF DESCRIPTION OF THE DRAWINGS

FIG. 1 is a surface acoustic wave interferometer vapor sensor.

FIG. 2 shows an expanded view of the gas jet nozzle and surface acoustic wave interferometer of the invention.

REFERENCE NUMERALS IN DRAWINGS

10 Piezoelectric Crystal

Figure 3A:
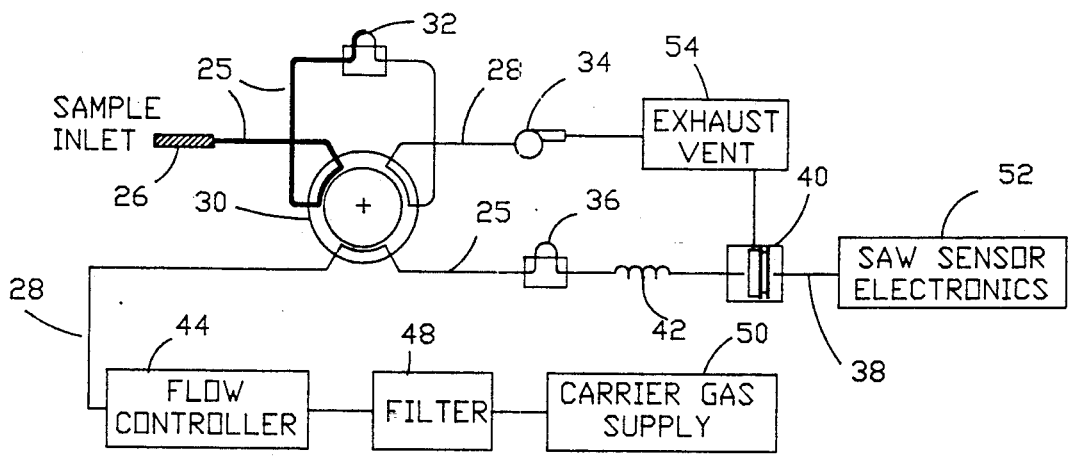
FIG. 3 shows operating method of the vapor detection apparatus: 3A shows the apparatus in the sample collection position, 3B shows the apparatus in the sample transfer position and 3C shows the apparatus in the inject and analysis position.

12 Reflector Array
14 Reflector Array
16 Reflector elements
18 Input Idt
20 Output Idt
22 Idt bond pad
23 Ribbon bond wire
24 Adsorption area
25 Quartz tubing
26 Sample inlet port
28 SS tubing
30 GC 6 port valve
31 Valve Actuator
32 Concentrator tube
33 Insulating standoff
34 Rotary Vane Pump
36 Focus concentrator
38 Electrical cable
40 SAW Sensor assembly
42 GC Separation column
44 Gas flow controller
48 Gas filter
50 Carrier Gas supply
52 Sensor electronics
54 Vented exhaust
56 Thermoelectric cooler
60 Nozzle flow lines
62 Nozzle alignment block
64 Inner Nozzle sleeve
65 Outer Nozzle sleeve
66 Qtz Capillary Nozzle
68 GC gas fitting
70 Heat sink
72 Heat radiator
74 Circuit board
76 Cooling Fan
78 Mounting Block
82 Temperature plot
84 Frequency plot
86 Adsorption Chromatogram
88 User notes
92 Desorption Chromatogram

DETAILED DESCRIPTION OF A PREFERRED EMBODIMENT

The preferred embodiment of the invention uses a surface acoustic wave interferometer as shown in FIG. 1. The SAW interferometer consists of at least two reflecting arrays 12,13 of reflecting elements 16 which act to reflect surface acoustic waves launched from one or more interdigital metal electrodes 18,20 defined on the surface of a piezoelectric crystal 10. At a frequency of resonance, constructive interference between surface acoustic waves reflected by the reflecting arrays produces an area 24 containing standing waves of high intensity and located between the two reflecting arrays. The interdigital electrodes piezoelectrically couple electrical energy into and out of the standing waves of the acoustic interferometer and provide a means of detecting adsorbed vapors on the surface of the piezoelectric crystal 10.

In the preferred embodiment an inert gas containing chemical vapors is passed through a heated nozzle 66 so as to create a small and well confined gas jet 60. The gas jet is directed onto the surface area 24 of the SAW interferometer containing the high intensity acoustic standing waves as shown in FIG. 2. Helium gas is used in the preferred embodiment. The collection area 24 of the SAW interferometer is held in close proximity to the He jet 60 of the nozzle 66. The nozzle is constructed of quartz capillary tubing 0.30 mm inside diameter. The preferred embodiment maintains the nozzle temperature at 200° C. so as to prevent adsorption of chemical vapors entrained in the He gas flowing through the nozzle orifice. The quartz capillary of the nozzle is conductance heated by an inner copper sleeve 64 and an outer stainless steel tube. Condensible vapors within the He jet condense onto the surface of the acoustic interferometer and their physical properties alter the amplitude and phase of the standing acoustic waves.

Gold ribbon bonding wires 23 are used to connect the bonding pads 22 of the interdigital electrodes to an electronic circuit board containing an amplifier. As is known amongst those who practice the Art of Oscillator design, an amplifier with sufficient gain to overcome the losses within the standing waves of the interferometer and the proper phase to reinforce said waves will maintain said wave amplitude and generate an oscillation frequency exactly equal to that of the interferometer standing waves.

The quantity of material condensed or adsorbed from the condensible vapors entrained within the gas jet 60 nozzle is determined by the vapor pressure of the individual vapor species and the surface temperature of the condensing surface 24. In the preferred embodiment the temperature of the surface wave interferometer is controlled by passing an electrical current through a thermoelectric device 56 attached to the back surface of the piezoelectric crystal.

The thermoelectric device consists of a ferroelectric ceramic material, typically barium titanate, which creates heat flow in proportion to the direction and amount of electric current passing through it. The other surface of the thermoelectric device is attached to a thermal heat sink 70. The heat sink provides a thermal conduction path to radiating fins 72 and a fan 76 for removing or supplying heat to the thermoelectric device and its thermal load.

In the preferred embodiment the temperature of the SAW interferometer surface is controlled by passing an electric current through the thermelectric material attached to the back side of the piezoelectric crystal 10. A computer is used to select the amount of heating or cooling of the interferometer surface produced by the thermoelectric material. By controlling the temperature of the surface acoustic wave interferometer, conditions inducing the adsorption of favored vapor species and not others can be created. The vapor pressure of each vapor species varies from high for volatile vapors to low for sticky vapors. By selecting the proper surface temperature, vapors more volatile relative to the desired material are not detected.

Adsorbed vapors on the surface of the acoustic interferometer do not change the physical properties of the piezoelectric crystal surface. Unlike absorption, adsorbed vapors form a thin upper layer of condensed vapor material on top of the piezoelectric surface and the acoustic wave must propagate through the resulting layered propagation media. The physical parameters used in prior art identification methods have been the equilibrium concentration of a chemical vapors diffused into polymer coatings as measured by monitoring the change in resonant frequency or rate of diffusion produced by a shift in phase as an acoustic wave passed through a single pass delay line.

In the preferred embodiment, vapors need not be absorbed on the surface of the crystal surface and an absorbing polymer material is not required to produce a specific response characteristic for individual vapor species. The invention creates a vapor specific response by using a temperature gradient selectively induce adsorption or condensation. Furthermore, in this embodiment of the invention, the rate of adsorption is controlled by the temperature gradient, the vapor pressure of each vapor species, and the thermal conductivity of the carrier gas jet.

Prior art identification methods used a one way transmission of a surface acoustic wave through a physically altered portion of an acoustic delay line and a measurement of the resulting phase shift of the wave. However, this preferred embodiment uses an interferometer where the phase of the acoustic wave is shifted multiple times as it is reflected from one interferometer reflector array to another and then back again. Because the wave passes many times through the adsorbed layer the phase shift is much larger than previous delay line sensors. The resulting acoustic phase shift is translated into a frequency shift by piezoelectric interdigital transducers controlling the electronic oscillations that are created by using the SAW interferometer as the positive feedback element of a high frequency amplifier. The frequency of the oscillations are counted and the instantaneous frequency of the oscillation is proportional to the total amount of material adsorbed on the surface of the interferometer.

SAW devices in prior art chemical sensors only used the rate of diffusion and equilibrium concentration of a diffused species to identify said species. In Prior Art only physical changes resulting from absorption were used. However, in this embodiment the identification of a particular species is made possible by a measurement of the rate of desorption during a programmed temperature rise of the SAW interferometer. Desorption from a heated surface is governed by an exponential rate of desorption as a function of temperature. The desorption rate is generally different for each vapor species. In this embodiment the SAW sensor temperature is programmed to a value $T_1=0°$ C. which results in 100% adsorption of all condensible vapor species in the gas jet. When the SAW temperature is linearly increased to a temperature $T_2=120°$ C. at a rate of 2.5° per second, complete desorption of all vapor species occurs. Between temperature $T_1$ and temperature $T_2$ the individual species evaporate from the surface at different rates. The more volatile species or higher vapor pressure materials desorb from the surface wave interferometer vapor sensor first at the lower temperatures of the programmed temperature rise and lower vapor pressure materials the desorb from the sensor surface at later time or higher temperatures. A measurement of the surface wave interferometer frequency during desorption of each material allows a determination of the individual vapor species or groupings of vapor species present in the vapor jet according to their rate of desorption.

Figure 4:
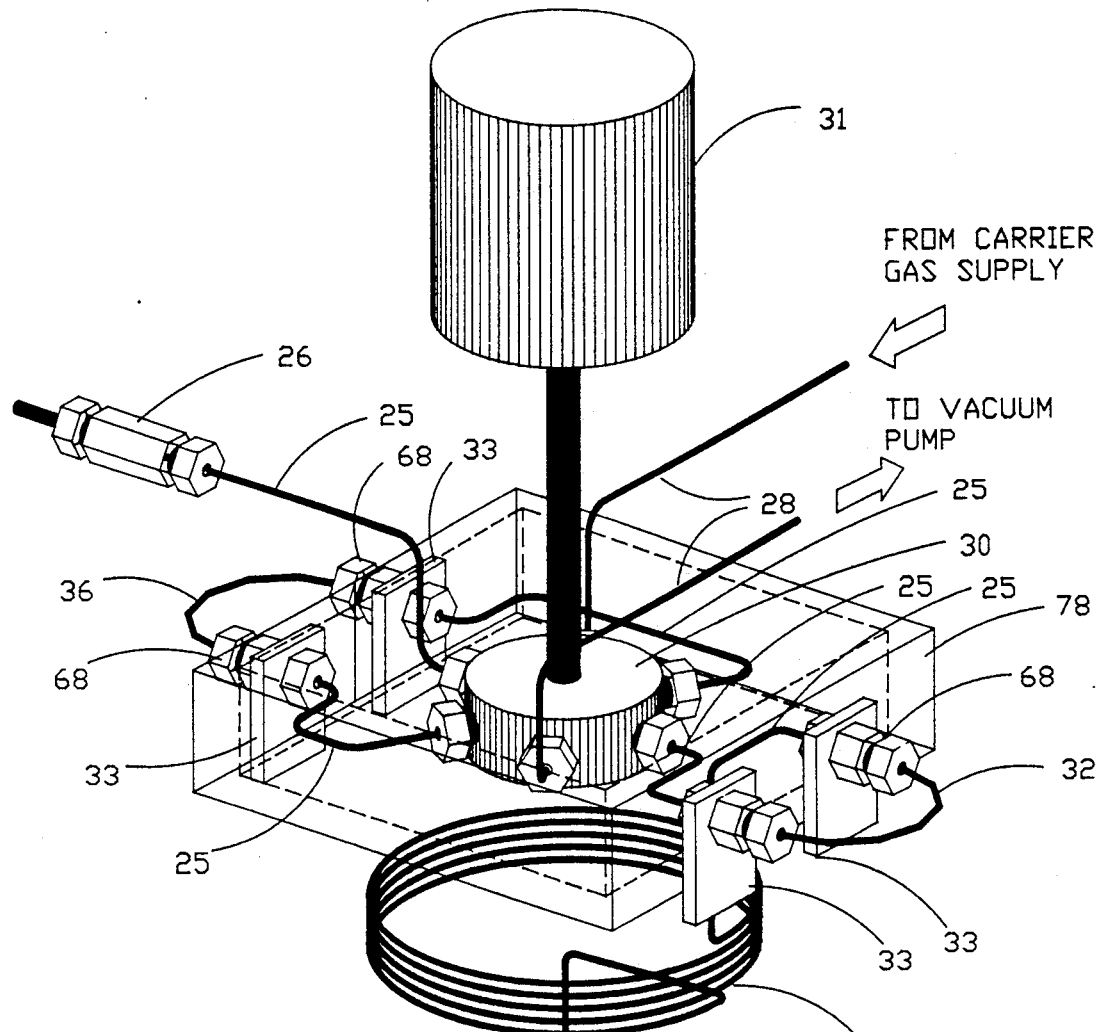
FIG. 4 shows a preferred embodiment of the invention.
Figure 5:
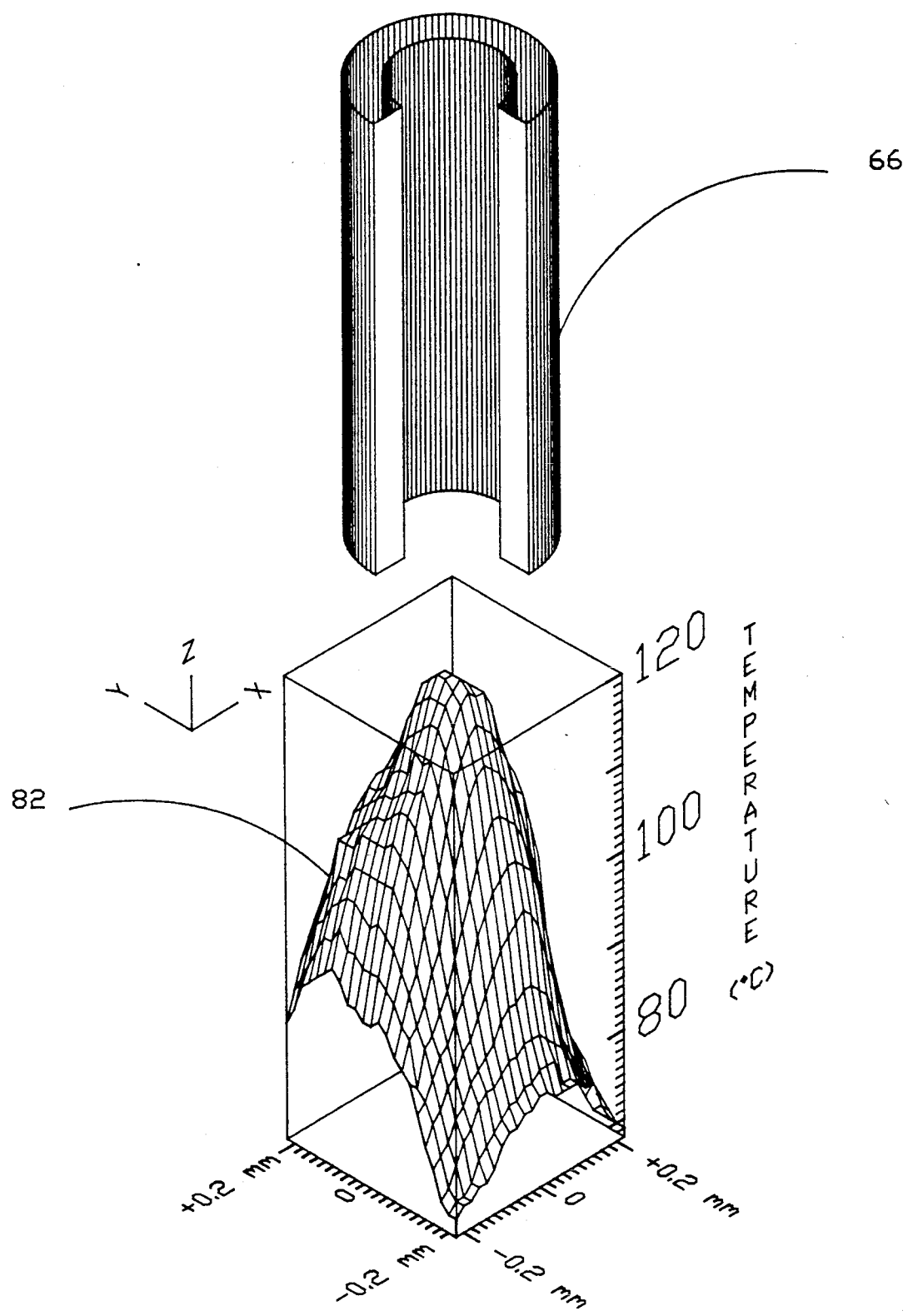
FIG. 5 shows a three dimensional plot of the temperature gradient within the exit gas of the nozzle.
Figure 6A:
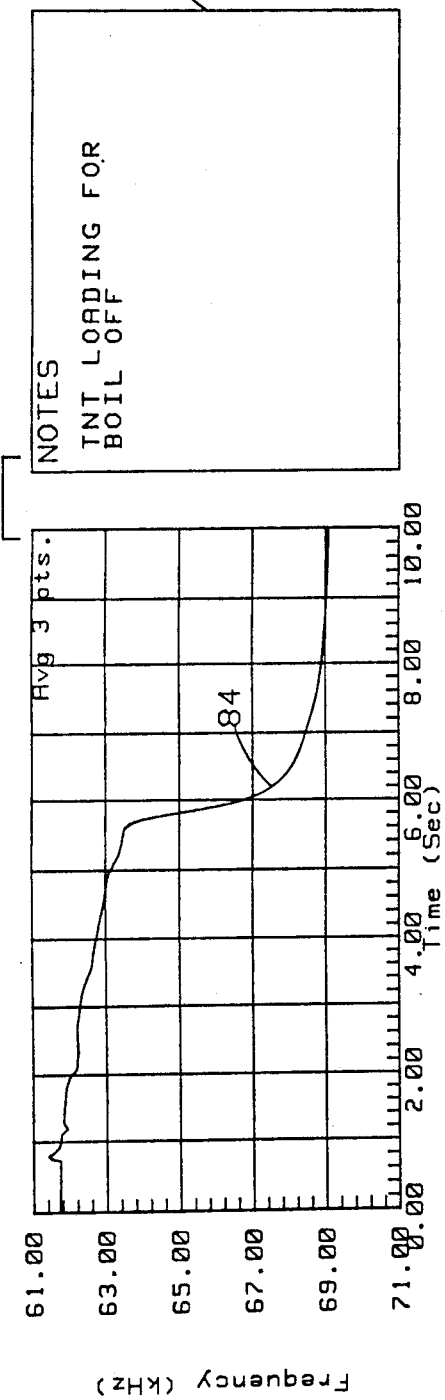
FIG. 6 shows an adsorption chromatogram of the vapor detection apparatus.
Figure 6B:
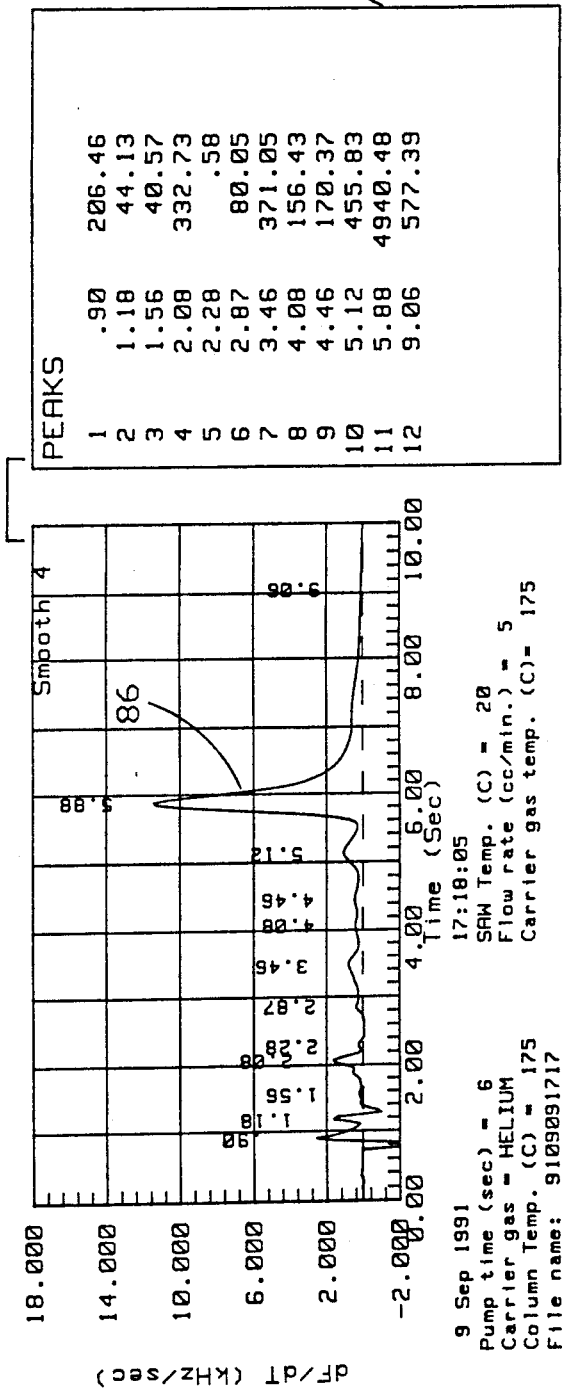
Figure 7:
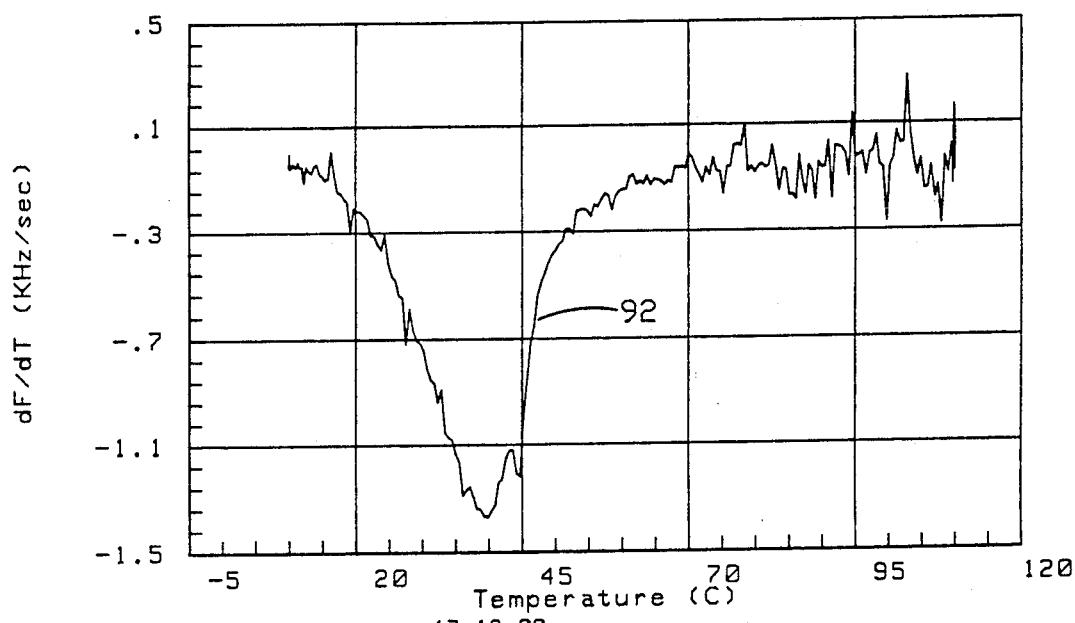
FIG. 7 shows a desorption chromatogram of the vapor detection apparatus.

Another object of the present invention is a method and apparatus for collecting condensible vapors present in one gaseous atmosphere and efficiently transferring and injecting said condensible vapors into a another gas atmosphere in the form of a burst of vapors occupying a short period of time. An example of first embodiment of the vapor collector and injector invention as well as a first embodiment of the acoustic interferometer detector invention is illustrated in FIG. 4. The apparatus utilizing the detection method of the present invention and has a heated sample inlet 26 for admitting a sample to be analyzed to a stainless steel 25 flow line connected to one inlet of a six port gas chromatography valve 30. Attached to another port of the chromatography valve is a pipe connected to a source of filtered inert helium carrier gas at a controlled pressure of 10 psi. Attached to another port of the chromatography valve is a pipe connected to a vacuum pump. The vacuum pump must produce sufficient air flow through the inlet to collect condensible vapors within a reasonable time. The preferred embodiment uses a vacuum pump capable of producing an inlet flow rate of 50 cc per second of air. Individual valve ports are interconnected by a sealed grooved concentric shaft which is turned by a solenoid actuated pneumatic valve actuator 31. The apparatus is interconnected by stainless steel 2 mm inside diameter and quartz 0.3 mm inside diameter capillary tubing 28. Sampled inlet gas is passed through a cooled short tube 32 herein called the concentrator trap where condensible vapor is adsorbed and is concentrated. In the method to be described the adsorbed vapor is desorbed and re-adsorbed on another cooled tube 36 herein called the injector. The object of the injector is to quickly release or inject adsorbed vapors into an inert carrier gas flowing through a chromatographic separation column 42 consisting of a 0.3 mm inside diameter quartz capillary containing an absorbant chromatographic material. The individual vapor species within the carrier gas flow through the separation column at different velocities. The exit gases of the separation column then flow through the nozzle heater and alignment block 62 and exit the nozzle and are detected by the acoustic wave interferometer detector assembly 40. The concentrator trap, chromatography valve, injector, and separation column are confined within a thermally insulated and electrically heated aluminium oven housing 78 which maintains a temperature of 200° C.

In an example of a preferred embodiment the concentrator trap 36 and injector 32 include a 2.5 cm section of 30% copper-70% nickel capillary tubing having an inside diameter of 0.3 mm and an outside diameter of 0.35 mm inside diameter. The concentrator metal capillary section is connected to two ports of the six port chromatography valve by means of capillary pipe fittings 68 which are electrically and thermally insulated by means of ceramic attachment blocks 33. One end of the injector section is connected to one port of the chromatography valve and the other is connected to the quartz capillary separation column 42 by means of capillary pipe fittings 68 which are electrically and thermally insulated by means of ceramic attachment blocks 33. The concentrator section and injector section are external to the heated aluminium housing 78 and are exposed to ambient room air flow at a nominal temperature 25° C. A pair of copper wires are attached to each end of the concentrator capillary section. The wires are connected to an electronic pulse generator. In the same manner a pair of copper wires are attached to each end of the injector capillary section and connected to another electronic pulse generator. Both pulse generators are controlled by a microprocessor which provides separate accurately timed trigger signals to the pulse generators causing the pulse generator to apply a 50 ampere 0.001 second duration current pulse which flows through the concentrator or injector section as determined by which generator is triggered. The short duration current pulse causes heating of the copper nickel capillary which raises its temperature to 200° C. within 0.002 seconds. Rapid heating of the capillary section causes the absorbed vapors within the capillary to rapidly desorb into the ambient gas within the capillary section.

The acoustic wave interferometer detector assembly 40 contains a surface wave interferometer on the surface of a piezoelectric crystal 10 attached to a thermoelectric material 56. Surrounding the piezoelectric crystal is a copper circuit board 74. The circuit board and thermoelectric material are attached to a copper heat sink 70 with radiating fins 72 and a fan 76 to create a flow of ambient air over the radiating fins. Wires attached to the bonding pads of the interdigital acoustic wave transducers are attached to the circuit board 74 containing an electronic amplifier of the proper gain and phase so as to produce an oscillation frequency as described above. One end of a shielded cable and passing through the copper heat sink is attached to the oscillator circuit on the circuit board so as to cause part of the electrical oscillation current to flow to the other end of the cable which is attached to a frequency counter. The frequency counter is connected by means of an IEEE-488 parallel digital interface to the system computer.

In a similar manner a chromal-alumel thermocouple is attached by contact cement to the piezoelectric crystal and two wires from the thermocouple attached to a cable which passes through the copper heat sink. The other end of the cable is attached to a voltmeter connected to the system computer where thermocouple voltage is converted to temperature.

In a similar manner two wires are bonded to each surface of the thermoelectric material are attached to a cable which passes through the copper heat sink. The other end of the cable is attached to a electrical current generator capable of producing 1 ampere of current in either direction through the thermoelectric material. The current generator is connected by an IEEE-488 parallel digital interface to the system computer. By causing a positive current to flow in the thermoelectric material cooling of the piezoelectric crystal is achieved and reversing the current flow produces heating of the piezoelectric crystal.

The system computer provides for electrical control and timing of the chromatography valve actuator 31, concentrator capillary section heating current, injector capillary section heating current, oven housing 78 temperature, nozzle heater block 62 temperature, and piezoelectric crystal 10 temperature. The system computer records the oscillator frequency and system temperatures in a manner so as to detect and identify individual vapor species by frequency changes which occur when the vapor species are absorbed and desorbed from the surface of the piezoelectric crystal.

OPERATION

Figure 3B:
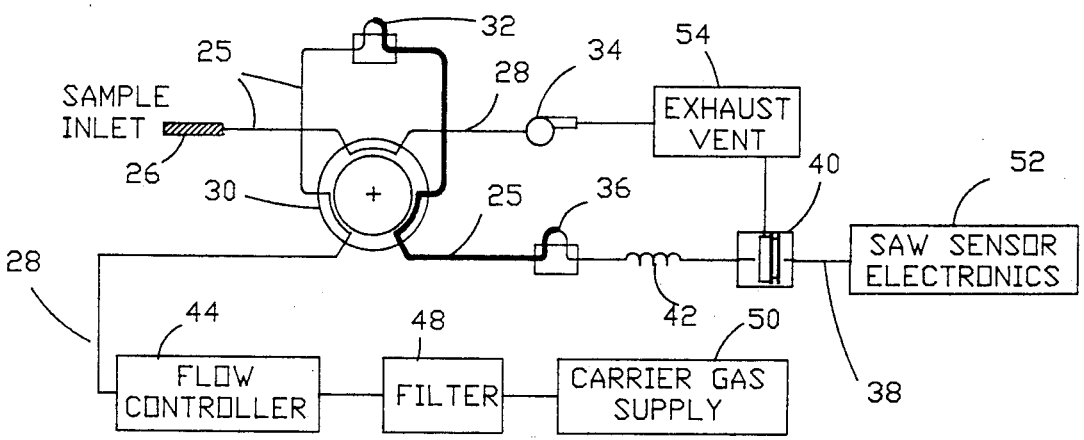
Figure 3C:
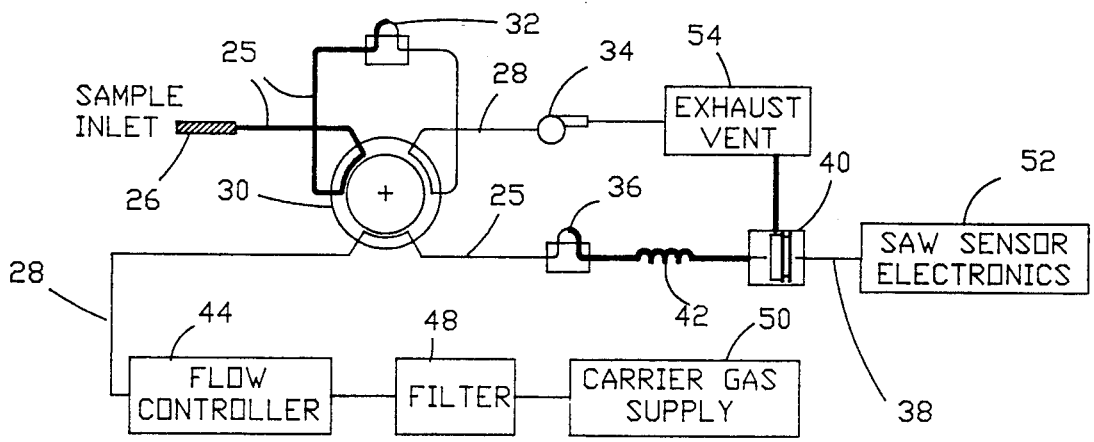

The operation of the vapor detection and identification apparatus is illustrated in FIGS. 3A, 3B and 3C. Operation begins with the chromatography valve 30 set in the collection position shown in FIG. 3A. A sample of the inlet 26 gas atmosphere and any condensible vapors contained therein are made to pass by means of a vacuum pump 34 through the concentrator section 32 which is cooled by ambient air flow to a temperature sufficient to adsorb condensible vapor species. The apparatus works with any ambient atmospheric gas, although air is the most common gas to be searched for specific condensible vapor species.

During a 5 to 30 second sampling time, a carrier gas supply 50 causes helium gas to flow through a filter 48 and a flow controller 44 after which it is passed through the chromatography valve 30, the injector section 36, the capillary separation column 42, the heated flow jet nozzle 66, and strikes the collection surface of the piezoelectric crystal 10. The preferred carrier gas is helium although the system will operate with any inert carrier gas. During the initial collection cycle the acoustic interferometer sensor temperature is raised by heat from a thermoelectric element 56 to a temperature of 120° C. sufficient to clean the sensor crystal surface by causing all adsorbed vapors to desorb and pass out through an exhaust vent 54. After the sample collection time has expired, the vacuum pump is turned off, the acoustic wave interferometer temperature is reduced to a temperature of 5° C. sufficient to induce adsorption, and the chromatography valve is switched to the transfer position shown in FIG. 3B. After the chromatography valve has switched to the transfer position the helium carrier gas flows through the concentrator section 32, the chromatography valve 30, the injector section 36, the capillary separation column 42, and through the acoustic interferometer assembly 40 to the exhaust vent. At this time a short 0.0025 second pulse of electrical current is made to flow through the concentrator section which rapidly raises it temperature to 200° C. and results in desorption of the trapped vapor species into the carrier gas. The carrier gas carries these desorbed vapors through the heated chromatography valve to the cooled injector section where the vapor species again condense and are trapped. Immediately Following the heating of the concentrator section is a cooling of period of from 1 to 10 seconds where the concentrator section is cooled back to ambient temperatures by conduction and radiation of the ambient air on the outer surface of the concentrator section.

Following the transfer cycle the chromatography valve is returned to the sample position. The preferred time for transfer is 1 second. After the transfer, a third cycle illustrated in FIG. 3C, the inject and analysis cycle is initiated. In this cycle a new inlet sample vapor is condensed onto the concentrator section while at the same time the injector section is heated by a precisely timed 0.001 second electrical current which rapidly heats the Cu-Ni tube of the injector section and causes the adsorbed vapor species to be rapidly desorbed and injected into the carrier gas flowing through the capillary separation column. The rapidly desorbed vapors are injected into the capillary separation column as a injection burst of vaporous material.

As is well known to practitioners of the gas chromatography, individual vapor species passing through a separation column travel at different velocities and hence individual vapor species exit the GC column at different times. The preferred embodiment uses a 36 inch length of 0.008 inch inside diameter quartz capillary coated with 5% phenyl phase (DB-5) bonded to the backbone silicon atoms of a polysiloxane stationary phase polymer. The capillary separation column is commercially available from J&W Scientific, Folsom, Calif. The preferred embodiment maintains the capillary column at a temperature of 200° C. and all vapor species exit the column within a time span of 5-10 seconds.

The gas flow passes through the separation column to a nozzle which causes the individual vapor species to be focused onto a geometrically confined and focused area of the acoustic wave interferometer where condensible vapor species are condensed due to the temperature gradient between the vapor stream and the collection surface. Uncondensed vapors pass on to the exhaust vent. An important feature of the invention is that the temperature gradient between the nozzle gas temperature and the piezoelectric crystal be sufficiently large so that all of the condensible vapors are collected and focused into an area of maximum amplitude standing acoustic waves on the crystal surface. Shown in FIG. 5 is a three dimensional plot of gas temperature 82 of exit gas from a 0.25 mm inside diameter nozzle 66 as measured 1 mm away from the nozzle exit orifice. The sharp drop in flow temperature on all sides of the flow jet is indicative of a well focused jet and produces a sharp temperature gradient on the surface of the piezoelectric crystal which causes any condensible vapors to be condensed within a small and well defined area on the piezoelectric crystal surface.

The preferred method of operation is to detect and record the frequency changes resulting from all adsorbed gas species during a time period long enough for all vapor species to exit the apparatus nozzle. This method is carried out by the measurement electronics 52 of the apparatus which comprises a frequency counter, system voltmeter, and a system computer. A histogram plot 84 of acoustic interferometer frequency vs time when atmospheric vapors containing trinitrotoulene are sampled as produced by the system computer is shown in FIG. 6A. The histogram data is differentiated so as to produce a related derivative histogram called an adsorption chromatogram 86 showing the rate of adsorption and desorption for each species detected, as shown in FIG. 6B. Wherever a peak occurs within the chromatogram a specific vapor species is detected. The system computer provides on screen operator notes 88 and a list 90 of all peaks, peak time delay relative to the injector section heating current pulse, and the total frequency change which was caused by adsorption of the specific vapor. The total frequency change is a measure of the concentration of each individual vapor species present in the sampled atmosphere.

Still another method of detection and analysis occurs at the end of the adsorption chromatogram and this method results in what is called a desorption chromatogram. While prior art has utilized selective adsorption with polymer coated surfaces at constant temperature, the desorption method causes the desorption of a chemical species to take place in a controlled manner using a linear rise in the temperature of the adsorbing surface. In the desorption method an electrical current is made to flow through the thermoelectric material 56 attached to the base of the piezoelectric crystal 10 in a manner which causes the temperature of the upper surface of the crystal containing the adsorbed vapors to rise in a linear manner. During the linear rise in temperature individual vapor species are desorbed at different rates and the desorption of each species is detected as a rise in the acoustic wave interferometer frequency. A desorption chromatogram obtained with the preferred apparatus embodiment described above is shown in FIG. 7 and was recorded using a 2.5° C. per second temperature rise of the piezoelectric crystal. The rate of desorption for an individual species increases exponentially with increasing temperature until all of the vapor species is desorbed from the surface causing an abrupt cessation of frequency change. Specific vapor species or groups of vapor species are identified by their rate of desorption. This method results in information which when combined with the adsorption chromatogram method provides a clear identification of the vapor species and their concentration in the inlet sample atmosphere.

After all of the adsorbed vapors have been desorbed from the surface of the piezoelectric crystal the electrical current through the thermoelectric material is reversed causing the temperature of the piezoelectric crystal to drop back to the original temperature selected for adsorption. The desorption method thus has the advantage over prior art of producing a clean crystal surface for each measurement. After the temperature of the crystal has reached the proper temperature for desorption the transfer and inject cycle is repeated and another burst of vapor is detected and analyzed by the vapor detection apparatus.

SUMMARY, RAMIFICATIONS, AND SCOPE

In accordance with the present invention, apparatus is provided for rapidly detecting and identifying a chemical vapor within an ambient atmosphere. The apparatus includes a means of collecting and transferring by injection collected vapors from one atmosphere to another containing a chromatography separation medium. The chromatography separation medium causes vapor species injected into an inert and flowing carrier gas to exit the separation medium delayed by a time characteristic of individual vapors. Passage through the separation medium is detected by directing gas containing condensible vapors onto the surface of a sensor by means of a nozzle which confines and focuses the adsorbed vapors to a specific location upon the surface of the crystal.

The sensor may preferably comprise a surface acoustic wave device having a plurality of reflecting elements which provide a means for creating constructive interference of propagating acoustic waves. The constructively interfering waves create standing acoustic waves and increase the sensitivity of the sensor over prior art devices which use only propagating acoustic waves.

The invention includes a method for detecting and identifying particular chemical species from a group of chemical substances comprising by means of controlled desorption of adsorbed vapors in response to heating of the sensor in a prescribed manner such that the desorption characteristics of individual vapor species become apparent.

Although the chemical sensor in the preferred embodiment of the invention is a surface acoustic wave device, it should be apparent that any chemical sensor using constructively interferring acoustic waves to increase sensitivity to adsorption and desorption may be used.

While the present invention has been described with respect to preferred embodiments and modifications thereto, it will be understood by those of ordinary skill in the art that further modifications may be made within the scope of the claims that follow. Accordingly, the scope of the invention is not to be in any way limited by the disclosure of the preferred embodiments, but should be determined entirely by reference to the claims.

The embodiments of the invention in which an exclusive property or privilege is claimed are defined as follows:

1. Apparatus for rapidly detecting and identifying a chemical vapors, comprising:

(a) a sensor having a surface exposed to the chemical vapors,
(b) a coated tubular section containing an inner coating of absorbant material whereby said tubular section separates individual vapor species according to their velocity in passing through said tubular section,
(c) a nozzle for directing a flow of chemical vapors onto said surface whereby said vapors are concentrated onto a specific region of said surface,
(c) monitoring means, coupled to the sensor, for monitoring the change in the physical parameter associated with said surface due to adsorption of the chemical substance, producing an electrical signal indicative of said change,
(d) analysis means, connected to the monitoring means, for determining a predicted time constant for adsorption of the chemical substance as a function of the electrical signal well before the chemical substance is completely adsorbed onto said surface,
(e) identification means for identifying the chemical substance from said group of chemical substances based upon its predicted time of arrival at said sensor and its rate of adsorption at a specific sensor temperature both of which are generally characteristic of individual chemical substances.

2. The apparatus of claim 1, wherein the sensor comprises an acoustic wave device having a plurality of spaced reflecting elements disposed so as to form standing acoustic waves by means of constructive interference between oppositely propagating acoustic waves and thereby increase the detection sensitivity of said surface to adsorbed vapors.

3. The apparatus of claim 2, wherein the sensor comprises an acoustic wave device of a characteristic frequency, said frequency decreasing as vapors are adsorbed on at least one surface.

4. The apparatus of claim 1, wherein a method of introducing the vapor sample into the coated tubular section is by means of transferring the sample from one atmosphere to another atmosphere including the steps of:

(a) adsorbing condensible vapors from one flowing gas by means of sorption/desorption tubular section,
(b) a transferring means for moving the adsorbed vapor from said sorption/desorption tubular section with a different flowing gas than the first said tubular section.

5. The apparatus of claim 4, wherein the tubular sections are electrically conductive capillaries.

6. The apparatus of claim 5, wherein a means of rapid vapor injection into a gas flow confined within said tubular sections by passage of an electrical current through said tubular sections.

7. Apparatus for rapidly detecting and identifying a chemical substance, comprising:
(a) a sensor having a surface exposed to the chemical substance,
(b) monitoring means, coupled to the sensor, for monitoring the change in the physical parameter associated with said surface due to desorption of the chemical substance, producing an electrical signal indicative of said change,
(c) a means of changing the temperature of said surface in a prescribed way with time whereby physical changes as a function of time and temperature are made clear,
(d) analysis means, connected to the monitoring means, for determining a predicted time constant for desorption of the chemical substance as a function of the electrical signal well before the chemical substance is completely desorbed from said surface,
(e) identification means for identifying the chemical substance from said group of chemical substances based upon its predicted time constant for desorption which is generally characteristic of the chemical substance and different than those of other chemical substances of the group.

8. The apparatus of claim 7, wherein the sensor comprises an acoustic wave device having a plurality of spaced reflecting elements disposed so as to form standing acoustic waves by means of constructive interference between oppositely propagating acoustic waves and thereby increase the sensitivity of said surface to desorbed vapors.

* * * * *